United States Patent [19]

Soothill et al.

[11] 4,233,286

[45] Nov. 11, 1980

[54] LOW AFFINITY IGM-LATEX PARTICLES AND ASSAY THEREWITH FOR IMMUNE COMPLEXES

[75] Inventors: John F. Soothill; Roland J. Levinsky, both of London, England

[73] Assignee: National Research Development Corporation, London, England

[21] Appl. No.: 831,872

[22] Filed: Sep. 9, 1977

[30] Foreign Application Priority Data

Aug. 31, 1977 [GB] United Kingdom ............... 36364/77

[51] Int. Cl.² .................... G01N 21/00; G01N 23/00; G01N 31/00; G01N 33/16
[52] U.S. Cl. ................................. 424/12; 23/230 B; 424/8; 424/11; 424/13; 424/78; 424/85; 424/88; 424/101
[58] Field of Search ................... 424/8, 11, 12, 13, 78, 424/85, 88, 101; 23/230 B

[56] References Cited

U.S. PATENT DOCUMENTS

| | | | |
|---|---|---|---|
| 4,021,534 | 5/1977 | Lafontaine | 424/85 X |
| 4,062,935 | 12/1977 | Masson | 424/12 |
| 4,092,114 | 5/1978 | Buck | 424/12 X |
| 4,141,965 | 2/1979 | Soothill | 424/12 X |

OTHER PUBLICATIONS

Stone, The J. of Biol. Chem., vol. 243, No. 22, Nov. 25, 1968, pp. 5977–5984.
Ikeda, Chem. Abs., vol. 85, 1976, Ab. No. 76251h.
Franek, Chem. Abs., vol. 84, 1976, Ab. No. 119793k.
Kim, Chem. Abs., vol. 81, 1974, Ab. No. 150708c.
Petty, Chem. Abs., vol. 78, 1973, Ab. No. 41350t.
Steward, Chem. Abs., vol. 78, 1973, Ab. No. 27792g.
Gurvich, Nature, vol. 203, Aug. 8, 1964, pp. 648–649.
Lurhuma, Clinical & Exper. Immuno, vol. 25, 1976, pp. 212–226.
Eisenberg, Immuno Chem. 1976, vol. 13, 355–359.
Sobel, The J. of Exptl. Med., vol. 142, 1975, pp. 139–150.
Little, Methods in Immunol. & Immunochem., vol. I, 1967, pp. 128–133.
Van Oss, RES-The J. of The Reticuloendothelial Soc., vol. 3, 1966, pp. 29–40.
Holborow, Immunol. in Med. Acd. Press, London 1977, pp. 544, 545.
White, et al., Essentials of Immunol & Micro, Pitman Medical, London, 1973, pp. 89–105.
Schmidt, Chem. Abs., vol. 88, 1978, Ab. No. 35692w.

*Primary Examiner*—Anna P. Fagelson
*Attorney, Agent, or Firm*—Oblon, Fisher, Spivak, McClelland & Maier

[57] ABSTRACT

A method for the estimation of an immune complex and analysis of a constituent thereof comprising a latex particle agglutination test, in which a sample containing immune complex is incubated with latex particles coated with low affinity non-human antibodies to said complex constituent.

14 Claims, No Drawings

LOW AFFINITY IGM-LATEX PARTICLES AND ASSAY THEREWITH FOR IMMUNE COMPLEXES

The present invention relates to the estimation of immune complexes and analysis of constituents thereof.

Immune antigen-antibody complexes have been implicated in the pathogenesis of many human diseases, and thus their detection and estimation is of central importance to the treatment of these diseases.

Our co-pending application, United Kingdom Patent Application No. 48995/76, describes a method for the estimation of an immune complex and analysis of a constituent thereof, in which sample containing immune complex is incubated with coated latex particles and IgM antibodies, the latex particles coated with said complex constituent and the IgM antibodies being low affinity non-human IgM antibodies to said complex constituent. The method constitutes a latex particle agglutination test in which presence of appropriate immune complexes in the sample is determined by their inhibition of agglutination of the coated latex particles, and this inhibition of agglutination may be monitored by use of a suitable electronic particle counting apparatus such as a Coulter counter.

A modified technique has now been devised for estimation of an immune complex and analysis of a constituent thereof.

Accordingly a method for the estimation of an immune complex and analysis of a constituent thereof comprises a latex particles agglutination test, in which a sample containing immune complex is incubated with latex particles coated with low affinity non-human IgM antibodies to said complex constituent.

Any constituent of the immune complex may be analysed by the present method, provided the constituent can be used to produce low affinity non-human IgM antibodies and provided these antibodies are capable of attachment to latex particles. Thus the immunoglobulin consituent e.g. IgG or IgA, or complement components e.g. $C_3$, of complex may be analysed by the present method. The method may also be employed for analysis of antigen constituents of complex, for instance for analysis of viral, bacterial or other antigenic materials giving rise to complex formation.

Immune complexes are believed to cause disease symptoms, especially tissue damage, and thus the method may be employed for diagnosis of immune complex associated diseases. In a preferred embodiment the method may provide a simple and easily applied test e.g. a slide agglutination test, for such diagnosis and screening large populations for incidence of immune complex associated diseases. The method may also be used to monitor the effect of treatment e.g. chemotherapy or plasmapheresis, upon the levels of immune complex e.g. present in a patient's bloodstream.

The coated latex particles used in the method of the present invention are prepared by linking the low affinity non-human IgM antibodies to latex or similar particles, and are characteristically in a form suitable for latex particle agglutination tests. Some of these antibodies may undergo spontaneous attachment on contact with latex particles, though it may be desirable to employ a coupling reagent to link the antibodies to latex particles. Any suitable coupling reagent may be employed, such as carbodiimide.

It has been found, in a preferred embodiment according to the present invention, that dinitrophenol (DNP) substitution is particularly suitable for coating latex particles with low affinity non-human IgM antibodies. Generally, prior substitution of the IgM antibodies with DNP, for instance by use of the reagent monofluoro-2,4-dinitrobenzene, permits coating of latex particles with IgM antibodies which may otherwise resist attachment. Usually, 2, 4 dinitrophenol substitution is used, though other dinitrophenol substitution may also be employed.

The low affinity non-human IgM antibodies which are coupled to latex particles for use in the immune complex assay method are raised in suitable animals to the constituent of complex which is undergoing analysis. For laboratory purposes small animals such as guinea pigs or especially rabbits, have been found to be satisfactory for production of these antibodies, however larger animals such as sheep, cows or horses may be more desirable for large scale production. Generally the immune complex constituent, preferably in purified form, is injected into the animal, the animal subsequently bled and IgM separated out of the antiserum. Advantageously the yield of low affinity IgM may be optimised having regard to various factors as will be apparent to skilled workers in the art. For instance, the concentration of immune complex constituent injected into the animal, the use of adjuvants, and the site of injection may affect the subsequent yield of antibody. Especially also, the period allowed after injection and before bleeding of the animal may have a bearing upon the various antibody components present in the antiserum. A period of about ten days has been found to be appropriate for satisfactory low affinity IgM production in rabbits after injection with purified human immunoglobulin classes IgA, and IgG in Freund's complete adjuvant. Generally, it is also believed that similar periods are appropriate for satisfactory low affinity IgM production with other immune complex constituents.

Characteristically the low affinity non-human IgM antibodies interact specifically with the complex constituent to which they have been raised, and this interaction is typically readily reversable unless the constituent is in an aggregated form e.g. as a component of an immune complex. Thus, on incubation, the low affinity IgM antibody coated latex particles conveniently interact strongly with any immune complex present in the incubate comprising the particular constituent. Thus immune complexes may be estimated and their constituents analysed by the agglutination of latex particles which they cause, the greater the concentration of immune complex the greater the agglutination of the latex particles. For example, sample containing immune complex is mixed with the coated latex particles and incubated after which agglutination is monitored by any suitable technique.

Generally it is desired to determine immune complexes as a component of a patient's bloodstream, though the present invention may be equally well applied to the determination of immune complexes in other media including other physiological fluids such as urine. Thus samples derived from serum or other physiological fluid may require suitable preparation before use in the immune complex test; though unlike the method described in our co-pending application, U.K. patent application No. 48995/76 (corresponding to U.S. application Ser. No. 831,349, filed Sept. 7, 1977 now U.S. Pat. No. 4,141,965), the sample does not normally require decomplementing before the test.

After preparatory treatment, if required, samples e.g. serum samples, are mixed with the coated latex particles and incubated. The incubate is generally aqueous and incubation is carried out, preferably with agitation, for a period sufficient to complete reaction.

Subsequent to incubation the agglutination of latex particles may be monitored by any suitable means. For example, in a preferred embodiment, a simple slide agglutination procedure may be employed, conveniently relying upon a straightforward visual comparision. Alternatively, particularly where accurate determination is required, an electronic particle counting apparatus, such as Coulter counter (Coulter Electronics Ltd.), may be used, and, for instance, may advantageously be programmed to count unagglutinated particles only.

The coated latex particle products used in the method of the invention are novel per se and are included within the scope of the invention. These products characteristically comprise latex particles coated with low affinity non-human IgM antibodies to complex constituents. The products are typically in a form suitable for latex particle agglutination test; for example, a latex particle size of diameter about 1.5 μm may be desirable, particularly when using an electronic particle counting apparatus. Preferably, also, the coated latex particle products may comprise DNP substituted low affinity IgM antibodies.

The reagents for use in the immune complex assay of the present invention may be supplied to the user in the form of kits and such kits are included within the scope of the invention. Such kits typically comprise latex particles coated with low affinity non-human IgM antibodies to the constituent of complex undergoing analysis, and may also conveniently comprise appropriate buffer solutions for use in the method and possibly also suitable slides for use in the slide agglutination adaptation of the method. Generally, also, kits may be supplied for estimation of a range of different types of immune complex and analysis of a range of complex constituents and thus may comprise a corresponding range different latex particle reagents coated with the corresponding range of low affinity non-human IgM antibodies. Usually these kits are supplied together with instructions or other indications to enable the user to carry out the assay method which advantageously requires little laboratory experience.

The invention is further illustrated in the following non-limiting examples.

EXAMPLE 1—Antibody Production

Low affinity IgM antibodies to human immunoglobulin classes IgA, IgM and IgG, for use in the immune complex assay of the present invention, are prepared separately as follows. High purity IgA is derived from myeloma sera and IgG from pooled fresh frozen plasma by DEAE 52 ion exchange chromatography. 10 mg of each of the purified immunoglobulins in complete Freund's adjuvant is then injected subcutaneously at four different sites into rabbits which are bled 10 days after the first injection. The sera obtained are separated on a Sephadex G200 column and the IgM peaks collected and concentrated to starting volume by ultrafiltration. Light chain specificity, present in the IgM antisera so produced, is absorbed out by Sepharose (Fab')$_2$ immunosorbent columns to give monospecific antisera. The period of ten days between injection and bleeding is found to give reproducible yields of high titre but low affinity IgM antibodies containing no appreciable precipitating or high affinity antibody.

Low affinity IgM antibodies to other complex constituents are prepared by similar methods.

EXAMPLE 2—Coating of Latex Particles

IgM anti-human IgG 10 mg of purified low affinity IgM antibody to human IgG, as prepared in Example 1, in 1 ml of saline buffer is dialysed for 3 hours at 37° C. against 10% w/v sodium bicarbonate. 3 μl of monofluoro-2,4-dinitrobenzene is added and the reactants mixed constantly at 38° C. until a bright yellow colour is obtained, at which point the reaction is stopped by passing the reactants through a Sephadex G25 column and recovering the first fraction containing the DNP substituted material.

800 μl of a 10% w/v latex suspension (average particle diameter 1.15 μm) as supplied by Coulter Electronics, is washed twice in 1/5 strength 0.27 M glycine saline pH 8.2. The latex particles are separated from the wash liquid between and after washings by centrifuging at 10,000 rpm, and are finally resuspended in 20 ml of the 1/5 strength buffer. 40 μg of the DNP substituted low affinity IgM solution prepared above is then added per mg dry weight of latex and the whole mixed for 30–60 minutes at room temperature. The resultant IgM coated latex product is washed twice with the 1/5 strength buffer and resuspended in 20 ml of full-strength 0.27 M glycine saline buffer containing 0.1% human serum albumin (HSA) which blocks any free reactive sites remaining of the latex particles. The IgM coated latex particle suspension so obtained is suitable for estimation of immune complexes containing an IgG constituent.

Low affinity IgM antibodies to other constituents of complex, besides IgG, e.g. antigen constituents, are coated on to latex particles by similar methods.

EXAMPLE 3—Immune Complex Test

Serum samples from 4 patients are assayed for the presence of immune complexes by the method of the invention, using a simple slide agglutination technique.

Two of the serum samples are from healthy patients and are shown to contain no immune complexes by the inhibition of latex particle agglutination test of our co-pending application United Kingdom Patent Application No. 48995/76. The remaining two sera are from patients suffering from systemic lupus erythematosus (SLE), one with low levels of IgG complexes and the other with high levels of IgG complexes.

The serum samples are diluted 1:20 with glycine saline buffer, ph 8.2. 50 μl aliquots of the diluted sera are pipetted on to microscope slides each together with 50 μl of IgM anti-human IgG coated latex particle suspension, as prepared in Example 2. The slides are then gently rocked for 10 minutes, and the results observed are given in the table below. This table also includes quantitative results obtained by the inhibition of latex particle agglutination test mentioned above. Both healthy subjects show no agglutination after 10 minutes; whereas sera 3 and 4, from the patients with SLE, give positive agglutination reactions, the extent of which differ in parallel with the results obtained by the quantative test.

Table Latex slide agglutination test for IgG soluble complexes in serum. Visual assessment (scale 0—+ + + +) at 10 minutes. Serum 4 showed marked clumping at 10 minutes, and was the first to give detectable agglutination.

| Patient | Direct Slide Agglutination | Quantitative Inhibition of Agglutination Test |
|---|---|---|
| 1. Healthy | 0 | 8% (i.e. Normal up to about |
| 2. Healthy | 0 | 11% 20%) |
| 3. SLE (Minor Symptoms) | ++ | 31% |
| 4. SLE (Major Symptoms) | ++++ | 47% |

Complexed IgG present in the sera of the two sick patients binds to the IgM antibodies which are coated on the latex particles and thereby causes the latex particles to agglutinate.

Other constituents of immune complex, besides IgG, are assayed in a similar fashion, using latex particles coated with the corresponding low affinity non-human IgM antibodies.

As an alternative to the slide agglutination technique described above, a suitable electronic particle counting apparatus, such as a Coulter counter model ZB, is used to more accurately monitor the extent of agglutination of the latex particles.

We claim:

1. A method for the estimation of a human immune complex and analysis of an antibody constituent thereof comprising a latex particle agglutination test, in which a sample containing human immune complex is incubated with latex particles coated with low affinity IgM antibodies raised in a non-human animal against said human anitbody constituent.

2. A method according to claim 1, in which the complex constituent undergoing analysis is an immunoglobulin constituent of said complex.

3. A method according to claim 1, comprising a slide agglutination test.

4. A method according to claim 1, in which, subsequent to incubation, agglutination is monitored by means of an electronic particle counting apparatus.

5. The method of claim 1 wherein said human immune complex is from a sample of human blood.

6. The method of claim 1 wherein said human immune complex is from a sample of human urine.

7. A latex particle product coated with immunoglobulins consisting of low affinity IgM antibodies raised in a non-human animal against a human antibody.

8. The product of claim 7 wherein said latex particles have a dimeter of about 1.15 μm.

9. The product of claim 7 wherein said human antibody is human IgA.

10. The product of claim 7 wherein said human antibody is human IgG.

11. The product of claim 7 wherein said human antibody is human IgM.

12. The product of claim 7 wherein said non-human IgM antibodies are extracted from an animal selected from the group consisting of rabbits, guinea pigs, sheep, cows and horses.

13. The product of claim 12 wherein said animal is a rabbit.

14. The product of claim 12 wherein said animal is a guinea pig.

* * * * *